(12) United States Patent
Kang

(10) Patent No.: US 6,190,908 B1
(45) Date of Patent: Feb. 20, 2001

(54) MODULATION OF POLYPEPTIDE DISPLAY ON MODIFIED FILAMENTOUS PHAGE

(75) Inventor: Angray S. Kang, Carlsbad, CA (US)

(73) Assignee: The Scripps Research Institute, La Jolla, CA (US)

(*) Notice: Under 35 U.S.C. 154(b), the term of this patent shall be extended for 0 days.

(21) Appl. No.: 09/198,839

(22) Filed: Dec. 24, 1998

Related U.S. Application Data

(60) Provisional application No. 60/096,326, filed on Aug. 12, 1998.

(51) Int. Cl.⁷ .................................................. C12N 15/72
(52) U.S. Cl. ............................................................ 435/320.1
(58) Field of Search .......................... 435/6, 320.1, 691, 435/235.1

(56) References Cited

U.S. PATENT DOCUMENTS 5,427,908 * 6/1995 Dower et al. .............................. 435/5
5,658,727 * 8/1997 Barbas et al. ............................. 435/6

* cited by examiner

*Primary Examiner*—James Ketter
(74) *Attorney, Agent, or Firm*—Thomas E. Northrup

(57) ABSTRACT

A modified filamentous phage that contains a gene for a wild type phage coat protein and a gene for a synthetic phage coat protein is provided. Uses of the modified phage and kits containing the phage are also provided.

2 Claims, 8 Drawing Sheets tctagaGTTAATAACAAGGAGACAGTATCGATGAAAAAGACAGCTATCGCGATTG
CAGTGGCACTGGCTGGTTTCgctagcgtagctcagGCCGGCcAAGCTTCTGGCGCCGTCC
CTGCAGAAGGTGATGACCCGGCTAAAGCTGCTTTTGACTCTCTTCAGGCTTCTG
CTACTGAATACATCGGCTACGCTTGGGCTATGGTGGTTGTTATCGTTGGTGCTA
CTATTGGCATCAAACTTTTCAAAAAATTCACTTCTAAAGCGTCTTAATGAACTC
AGATACCCAGCCCGCCTAATGAGCGGGCTTTTTTTAAGCTAGTGATGGCGTTC
CTATTGGTTAAAAATGAGCTGATTTAACAAAAATTTAACGCGAATTTTAACA
AAATATTAACGTTTACAATTTAAATATTTGCTTATACAATCTTCCTGTTTTTGGG
GCTTTTCTGATTATCAACCGGGGTACATATGATTGACATGCTAGTTTTACGATT
ACCGTTCATCGATTCTCTTGTTTGCTCCAGACTCTCAGGCAATGACCTGATAGC
CTTTGTAGATCTCTCAAAATAGCTACCCTCTCCGGCATTAATTTATCAGCTAG
AACGGTTGAATATCATATTGATGGTGATTTGACTGTCTCCGGCCTTTCTCACCC
TTTTGAATCTTTACCTACACATTACTCAGGCATTGCATTTAAAATATATGAGGG
TTCTAAAAATTTTTATCCTTGCGTTGAAATAAAGGCTTCTCCCGCAAAAGTATT
ACAGGGTCATAATGTTTTTGGTACAACCGATTTAGCTTTATGCTCTGAGGCTTT
ATTGCTTAATTTTGCTAATTCTTTGCCTTGCCTGTATGATTTATTGGATGTTAAT
GCTACTACTATTAGTAGAATTGATGCCACCTTTTCAGCTCGCGCCCCAAATGAA
AATATAGCTAAACAGGTTATTGACCATTTGCGAAATGTATCTAATGGTCAAACT
AAATCTACTCGTTCGCAGAATTGGGAATCAACTGTTACATGGAATGAAACTTC
CAGACAC
CGTACTTTAGTTGCATATTTAAAACATGTTGAGCTACAGCACCAGATTCAGCAA
TTAAGCTCTAAGCCATCCGCAAAAATGACCTCTTATCAAAAGGAGCAATTAAA
GGTACTCTCTAATCCTGACCTGTTGGAGTTTGCTTCCGGTCTGGTTCGCTTTGAA
GCTCGAATTAAAACGCGATATTTGAAGTCTTTCGGGCTTCCTCTTAATCTTTTTG
ATGCAATCCGCTTTGCTTCTGACTATAATAGTCAGGGTAAAGACCTGATTTTTG
ATTTATGGTCATTCTCGTTTTCTGAACTGTTTAAAGCATTTGAGGGGGATTCAA
TGAATATTTATGACGATTCCGCAGTATTGGACGCTATCCAGTCTAAACATTTTA
CTATTACCCCCTCTGGCAAAACTTCTTTTGCAAAAGCCTCTCGCTATTTTGGTTT
TTATCGTCGTCTGGTAAACGAGGGTTATGATAGTGTTGCTCTTACTATGCCTCG
TAATTCCTTTTGGCGTTATGTATCTGCATTAGTTAATGTGGTATTCCTAAATCT
CAACTGATGAATCTTTCTACCTGTAATAATGTTGTTCCGTTAGTTCGTTTTATTA
ACGTAGATTTTTCTTCCCAACGTCCTGACTGGTATAATGAGCCAGTTCTTAAAA
TCGCATAAGGTAATTCACAATGATTAAAGTTGAAATTAAACCATCTCAAGCCC
AATTTACTACTCGTTCTGGTGTTTCTCGTCAGGGCAAGCCTTATTCACTGAATG
AGCAGCTTTGTTACGTTGATTTGGGTAATGAATATCCGGTTCTTGTCAAGATTA
CTCTTGATGAAGGTCAGCCAGCCTATGCGCCTGGTCTGTACACCGTTCATCTGT
CCTCTTTCAAAGTTGGTCAGTTCGGTTCCCTTATGATTGACCGTCTGCGCCTCGT
TCCGGCTAAGTAACATGGAGCAGGTCGCGGATTTCGACACAATTTATCAGGCG
ATGATACAAATCTCCGTTGTACTTTGTTTCGCGCTTGGTATAATCGCTGGGGGT
CAAAGATGAGTGTTTTAGTGTATTCTTTCGCCTCTTTCGTTTTAGGTTGGTGCCT
TCGTAGTGGCATTACGTATTTTACCCGTTTAATGGAAACTTCCTCATGAAAAAG
TCTTTAGTCCTCAAAGCCTCTGTAGCCGTTGCTACCCTCGTTCCGATGCTGTCTT
TCGCTGCTGAGGGTGACGATCCCGCAAAAGCGGCCTTTAACTCCCTGCAAGCC

FIG. 4A

TCAGCGACCG,AATATATCGGTTATGCGTGGGCGATGGTTGTTGTCATTGTCGGC
GCAACTATCGGTATCAAGCTGTTTAAGAAATTCACCTCGAAAGCAAGCTGATA
AACCGAT
ACAATTAAAGGCTCCTTTTGGAGCCTTTTTTTTGGAGATTTTCAACGTGAAAA
AATTATTATTCGCAATTCCTTTAGTTGTTCCTTTCTATTCTCACTCCGCTGAAAC
TGTTGAAAGTTGTTTAGCAAAACCCCATACAGAAAATTCATTTACTAACGTCTG
GAAAGACGACAAAACTTTAGATCGTTACGCTAACTATGAGGGTTGTCTGTGGA
ATGCTACAGGCGTTGTAGTTTGTACTGGTGACGAAACTCAGTGTTACGGTACAT
GGGTTCCTATTGGGCTTGCTATCCCTGAAAATGAGGGTGGTGGCTCTGAGGGTG
GCGGTTCTGAGGGTGGCGGTTCTGAGGGTGGCGGTACTAAACCTCCTGAGTAC
GGTGATACACCTATTCCGGGCTATACTTATATCAACCCTCTCGACGGCACTTAT
CCGCCTGGTACTGAGCAAAACCCCGCTAATCCTAATCCTTCTCTTGAGGAGTCT
CAGCCTCTTAATACTTTCATGTTTCAGAATAATAGGTTCCGAAATAGGCAGGGG
GCATTAACTGTTTATACGGGCACTGTTACTCAAGGCACTGACCCCGTTAAAACT
TATTACCAGTACACTCCTGTATCATCAAAAGCCATGTATGACGCTTACTGGAAC
GGTAAATTCAGAGACTGCGCTTTCCATTCTGGCTTTAATGAAGATCCATTCGTT
TGTGAATATCAAGGCCAATCGTCTGACCTGCCTCAACCTCCTGTCAATGCTGGC
GGCGGCTCTGGTGGTGGTTCTGGTGGCGGCTCTGAGGGTGGTGGCTCTGAGGG
TGGCGGTTCTGAGGGTGGCGGCTCTGAGGGAGGCGGTTCCGGTGGTGGCTCTG
GTTCCGGTGATTTTGATTATGAAAAGATGGCAAACGCTAATAAGGGGGCTATG
ACCGAAAATGCCGATGAAAACGCGCTACAGTCTGACGCTAAAGGCAAACTTGA
TTCTGTCGCTACTGATTACGGTGCTGCTATCGATGGTTTCATTGGTGACGTTTCC
GGCCTTGCTAATGGTAATGGTGCTACTGGTGATTTGCTGGCTCTAATTCCCAA
ATGGCTCAAGTCGGTGACGGTGATAATTCACCTTTAATGAATAATTTCCGTCAA
TATTTACCTTCCCTCCCTCAATCGGTTGAATGTCGCCCTTTTGTCTTTAGCGCTG
GTAAACCATATGAATTTCTATTGATTGTGACAAAATAAACTTATTCCGTGGTG
TCTTTGCGTTTCTTTTATATGTTGCCACCTTTATGTATGTATTTTCTACGTTTGCT
AACATACTGCGTAATAAGGAGTCTTAATCATGCCAGTTCTTTTGGGTATTCCGT
TATTATTGCGTTTCCTCGGTTTCCTTCTGGTAACTTTGTTCGGCTATCTGCTTAC
TTTTCTTAAAAAGGGCTTCGGTAAGATAGCTATTGCTATTTCATTGTTTCTTGCT
CTTATTATTGGGCTTAACTCAATTCTTGTGGGTTATCTCTCTGATATTAGCGCTC
AATTACCCTCTGACTTTGTTCAGGGTGTTCAGTTAATTCTCCCGTCTAATGCGCT
TCCCTGTTTTTATGTTATTCTCTCTGTAAAGGCTGCTATTTTCATTTTGACGTTA
AACAAAAAATCGTTTCTTATTTGGATTGGGATAAATAATATGGCTGTTTATTTT
GTAACTGGCAAATTAGGCTCTGGAAAGACGCTCGTTAGCGTTGGTAAGATTCA
GGATAAAATTGTAGCTGGGTGCAAAATAGCAACTAATCTTGATTTAAGGCTTC
AAAACCTCCCGCAAGTCGGGAGGTTCGCTAAAACGCCTCGCGTTCTTAGAATA
CCGGATAAGCCTTCTATATCTGATTTGCTTGCTATTGGGCGCGGTAATGATTCC
TACGATGAAAATAAAAACGGCTTGCTTGTTCTCGATGAGTGCGGTACTTGGTTT
AATACCCGTTCTTGGAATGATAAGGAAAGACAGCCGATTATTGATTGGTTTCTA
CATGCTCGTAAATTAGGATGGGATATTATTTTTCTTGTTCAGGACTTATCTATTG
TTGATAAACACGCGCGTTCTGCATTAGCTGAACATGTTGTTTATTGTCGTCGTC
TGGACAGAATTACTTTACCTTTTGTCGGTACTTTATATTCTCTTATTACTGGCTC
GAAAATGCCTCTGCCTAAATTACATGTTGGCGTTGTTAAATATGGCGATTCTCA
ATTAAGCCCTACTGTTGAGCGTTGGCTTTATACTGGTAAGAATTTGTATAACGC

FIG. 4B

```
ATATGATACTAAACAGGCTTTTTCTAGTAATTATGATTCCGGTGTTTATTCTTAT
TTAACGCCTTATTTATCACACGGTCGGTATTTCAAACCATTAAATTTAGGTCAG
AAGATGAAATTAACTAAAATATATTTGAAAAAGTTTTCTCGCGTTCTTTGTCTT
GCGATTGGATTTGCATCAGCATTTACATATAGTTATATAACCCAACCTAAGCCG
GAGGTTAAAAAGGTAGTCTCTCAGACCTATGATTTGATAAATTCACTATTGAC
TCTTCTCAGCGTCTTAATCT.AAGCTATCGCTATGTTTTCAAGGATTCTAAGGGA
AAATTAATTAATAGCGACGATTTACAGAAGCAAGGTTATTCACTCACATATATT
GATTTATGTACTGTTTCCATTAAAAAAGGTAATTCAAATGAAATTGTTAAATGT
AATTAATTTTGTTTTCTTGATGTTTGTTTCATCATCTTCTTTTGCTCAGGTAATTG
AAATGAATAATTCGCCTCTGCGCGATTTTGTAACTTGGTATTCAAAGCAATCAG
GCGAATCCGTTATTGTTTCTCCCGATGTAAAAGGTACTGTTACTGTATATTCAT
CTGACGTTAAACCTGAAAATCTACGCAATTTCTTTATTTCTGTTTTACGTGCTAA
TAATTTTGATATGGTTGGTTCASTTCCTTCCATAATTCAGAAGTATAATCCAAA
CAATCAGGATTATATTGATGAATTGCCATCATCTGATAATCAGGAATATGATGA
TAATTCCGCTCCTTCTGGTGGTTTCTTTGTTCCGCAAAATGATAATGTTACTCAA
ACTTTTAAAATTAATAACGTTCGGGCAAAGGATTTAATACGAGTTGTCGAATTG
TTTGTAAAGTCTAATACTTCTAAATCCTCAAATGTATTATCTATTGACGGCTCT
AATCTATTAGTTGTTAGTGCACCTAAAGATATTTTAGATAACCTTCCTCAATTC
CTTTCTACTGTTGATTTGCCAACTGACCAGATATTGATTGAGGGTTTGATATTTG
AGGTTCAGCAAGGTGATGCTTTAGATTTTTCATTTGCTGCTGGCTCTCAGCGTG
GCACTGTTGCAGGCGGTGTTAATACTGACCGCCTCACCTCTGTTTTATCTTCTG
CTGGTGGTTCGTTCGGTATTTTTAATGGCGATGTTTTAGGGCTATCAGTTCGCG
CATTAAAGACTAATAGCCATTCAAAAATATTGTCTGTGCCACGTATTCTTACGC
TTTCAGGTCAGAAGGGTTCTATCTCTGTTGGCCAGAATGTCCCTTTTATTACTG
GTCGTGTGACTGGTGAATCTGCCAATGTAAATAATCCATTTCAGACGATTGAGC
GTCAAAATGTAGGTATTTCCATGAGCGTTTTCCTGTTGCAATGGCTGGCGGTA
ATATTGTTCTGGATATTACCAGCAAGGCCGATAGTTTGAGTTCTTCTACTCAGG
CAAGTGATGTTATTACTAATCAAAGAAGTATTGCTACAACGGTTAATTTGCGTG
ATGGACAGACTCTTTTACTCGGTGGCCTCACTGATTATAAAAACACTTCTCAAG
ATTCTGGCGTACCGTTCCTGTCTAAAATCCCTTTAATCGGCCTCCTGTTTAGCTC
CCGCTCTGATTCCAACGAGGAAAGCACGTTATACGTGCTCGTCAAAGCAACCA
TAGTACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACT
TGATTTGGGTGATGGTTCACGTAGTGGGCCATCGCCCTGATAGACGGTTTTTCG
CCCTTTGACGTTGGAGTCCACGTTCTTTAATAGTGGACTCTTGTTCCAAACTGG
AACAACACTCAACCCTATCTCGGGCTATTCTTTTGATTTATAAGGGATTTTGCC
GATTTCGGAACCACCATCAAACAGGATTTTCGCCTGCTGGGGCAAACCAGCGT
GGACCGCTTGCTGCAACTCTCTCAGGGCCAGGCGGTGAAGGGCAATCAGCTGT
TGCCCGTCTCGCTGGTGAAAAGAAAAACCACCCTGGCGCCCAATACGCAAACC
GCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAA
TTGTGAGCGGATAACAATTTCACACAGGAAACAGC
```

FIG. 4C gaattcTGAAGCCTGCTTTTTTATACTAACTTGAGCGTCTAGAGTTAATAACAAGG
AGACAGTATCGATGAAAAAGACAGCTATCGCGATTGCAGTGGCACTGGCTGGT
TTCgctagcgtagctcagGCCGGCcAAGCTTccctggtcaccgtcagcagtggtggcggaCACCCAGAAA
CGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGA
ACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGA
ATGACTTGGTTGAGTACTCACCAGTCACAGAAAGCATCTTACGGATGGCATG
ACAGTAAGAGAATTATGCAGTGCTGCCATAACCATGAGTGATAACACTGCGGC
CAACTTACTTCTGACAACGATCGGAGGACCGAAGGAGCTAACCGCTTTTTGC
ACAATATGGGGGATCATGTAACTCGCCTTGATCGTTGGGAACCGGAGCTGAAT
GAAGCCATACCAAACGACGAGCGTGACACCACGATGCCTGCAGCAATGGCAA
CAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCG
GCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGAT
CGCTGAGATAGGTGCCTCACTGATTAAGCATTGGTAAgtcgactaataaAGCCCGCCT
AATCAGCGGGCTTTTTTTctcgggCCGCGTTGCTGGCGTTTTTCCATAGGCTCCGC
CCCCCTGACGAGCATCACAAAAATCGACGCTCAAGTCAGAGGTGGCGAAACCC
GACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTTG
CAAGCAGCAGATTACGCGCAGAAAAAAAGGATCTCAactGTTACACAACTCTTG
TAGCCGATTAATAAAGCGTGCAACATGGAAGCCATCACAAACTGCATGATGAA
CCTGTACTGAGAGCGGCAATAACAGTCTATCCCCTTCTTGCTGATATTTTGCCA
TTGTTATAATGGGTGCAAAATAATCGGTAAATTAGCAACATTTAAATTAAAG
CTATCAAAATTAACCCAAGGTAATGCTGAAATATTTAAATGATTTCTGGTGTT
ACCCCTTGAGGAAATAACTTGGTATCACTTTTATAACGTTCCATTACCGATAAA
TAATTCACCATAAATTGATCAATATCGGATGAGTATGGGCAACTCAGTGCTGA
AAATGTCTCTGTTTCTTGATGGAATACGGTGAATTGTGGaTCaACTGAATCCCAT
ACGATCAATTCATCATCTTTTATCGCCATTCTCAACTCATCAAATTGATTCACG
GCCTGAGCAATCAGATAGATCATTACCGGATAAAACTTATACGCTGAATCATC
CAATGACTTTTTTAACGTCGTGATATCAATTTTGCTTGTTAAGCTAAAACCACA
TGGTAAACGATGCCGATAAAACTCAAAATGCTCACGGCGAACCCAATTTTTTA
CATCAAATTTTGTATAGTTCATAATCGATCCCTTCTGAATTTTTATTTACTAAGA
ACCTATCCCAAAAGGATTTTATTCCAGACAATGATGCACAGGCAAGA

FIG. 5 gaattcTGAAGCCTGCTTTTTTATACTAACTTGAGCGTCTAGAGTTAATAACAAGG
AGACAGTATCGATGAAAAGACAGCTATCGCGATTGCAGTGGCACTGGCTGGT
TTCgctagcgtagctcagGCCGGCTGGTGGCGGTGGCTCCcAAGCTTccctggtcaccgtcagcagt
ggtggcggaCACCCAGAAACGCTGGTGAAAGTAAAAGATGCTGAAGATCAGTTGGG
TGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTAT
GTGGCGCGGTATTATCCCGTATTGACGCCGGGCAAGAGCAACTCGGTCGCCGC
ATACACTATTCTCAGAATGACTTGGTTGAGTACTCACCAGTCACAGAAAAGCA
TCTTACGGATGGCATGACAGTAAGAGAATTATGCAGTGCTGCCATAACCATGA
GTGATAACACTGCGGCCAACTTACTTCTGACAACGATCGGAGGACCGAAGGAG
CTAACCGCTTTTTTGCACAATATGGGGGATCATGTAACTCGCCTTGATCGTTGG
GAACCGGAGCTGAATGAAGCCATACCAAACGACGAGCGTGACACCACGATGC
CTGCAGCAATGGCAACAACGTTGCGCAAACTATTAACTGGCGAACTACTTACT
CTAGCTTCCCGGCAACAATTAATAGACTGGATGGAGGCGGATAAAGTTGCAGG
ACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGAT
GAACGAAATAGACAGATCGCTGAGATAGGTGCCTCACTGATTAAGCATTGGTA
AgtcgactaataaAGCCCGCCTAATCAGCGGGCTTTTTTTctcgggCCGCGTTGCTGGCG
TTTTTCCATAGGCTCCGCCCCCTGACGAGCATCACAAAAATCGACGCTCAAGT
CAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGTTAC
CTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAGGATCT
CAactGTTACACAACTCTTGTAGCCGATTAATAAAGCGTGCAACATGGAAGCCA
TCACAAACTGCATGATGAACCTGTACTGAGAGCGGCAATAACAGTCTATCCCC
TTCTTGCTGATATTTTGCCATTGTTATAATGGGTGCAAAATAATCGGTAAAATT
AGCAACATTTAAATTAAAGCTATCAAAATTAACCCAAGGTAATGCTGAAATAT
TTAAATGATTTTCTGGTGTTACCCCTTGAGGAAATAACTTGGTATCACTTTTATA
ACGTTCCATTACCGATAAATAATTCACCATAAATTGATCAATATCGGATGAGTA
TGGGCAACTCAGTGCTGAAAATGTCTCTGTTTCTTGATGGAATACGGTGAATTG
TGGaTCaACTGAATCCCATACGATCAATTCATCATCTTTTATCGCCATTCTCAAC
TCATCAAATTGATTCACGGCCTGAGCAATCAGATAGATCATTACCGGATAAAA
CTTATACGCTGAATCATCCAATGACTTTTTAACGTCGTGATATCAATTTTGCTT
GTTAAGCTAAAACCACATGGTAAACGATGCCGATAAAACTCAAAATGCTCACG
GCGAACCCAATTTTTTACATCAAATTTTGTATAGTTCATAATCGATCCCTTCTG
AATTTTTATTTACTAAGAACCTATCCCAAAAGGATTTTATTCCAGACAATGATG
CACAGGCAAGA

FIG. 6

SEQUENCE LISTING

<160> NUMBER OF SEQ ID NOS: 11

<210> SEQ ID NO 1
<211> LENGTH: 7083
<212> TYPE: DNA
<213> ORGANISM: Artificial Sequence
<220> FEATURE:
<223> OTHER INFORMATION: Description of Artificial Sequence: a modified
    filamentous phage

<400> SEQUENCE: 1

```
tctagagtta ataacaagga gacagtatcg atgaaaaaga cagctatcgc gattgcagtg      60
gcactggctg gtttcgctag cgtagctcag gccggccaag cttctggcgc cgtccctgca     120
gaaggtgatg acccggctaa agctgctttt gactctcttc aggcttctgc tactgaatac     180
atcggctacg cttgggctat ggtggttgtt atcgttggtg ctactattgg catcaaactt     240
ttcaaaaaat tcacttctaa agcgtcttaa tgaactcaga tacccagccc gcctaatgag     300
cgggcttttt tttaagctag tgatggcgtt cctattggtt aaaaaatgag ctgatttaac     360
aaaaatttaa cgcgaatttt aacaaaatat taacgtttac aatttaaata tttgcttata     420
caatcttcct gtttttgggg cttttctgat tatcaaccgg ggtacatatg attgacatgc     480
tagttttacg attaccgttc atcgattctc ttgtttgctc cagactctca ggcaatgacc     540
tgatagcctt tgtagatctc tcaaaatagc taccctctcc ggcattaatt tatcagctag     600
aacggttgaa tatcatattg atggtgattt gactgtctcc ggcctttctc acccttttga     660
atctttacct acacattact caggcattgc atttaaaata tatgagggtt ctaaaaattt     720
ttatccttgc gttgaaataa aggcttctcc cgcaaaagta ttacagggtc ataatgtttt     780
tggtacaacc gatttagctt tatgctctga ggctttattg cttaattttg ctaattcttt     840
gccttgcctg tatgatttat tggatgttaa tgctactact attagtagaa ttgatgccac     900
cttttcagct cgcgccccaa atgaaaatat agctaaacag gttattgacc atttgcgaaa     960
tgtatctaat ggtcaaacta aatctactcg ttcgcagaat tgggaatcaa ctgttacatg    1020
gaatgaaact tccagacacc gtactttagt tgcatattta aaacatgttg agctacagca    1080
ccagattcag caattaagct ctaagccatc cgcaaaaatg acctcttatc aaaaggagca    1140
attaaaggta ctctctaatc ctgacctgtt ggagtttgct tccggtctgg ttcgctttga    1200
agctcgaatt aaaacgcgat atttgaagtc tttcgggctt cctcttaatc tttttgatgc    1260
```

```
aatccgcttt gcttctgact ataatagtca gggtaaagac ctgattttg atttatggtc     1320 attctcgttt tctgaactgt ttaaagcatt tgaggggat tcaatgaata tttatgacga     1380
ttccgcagta ttggacgcta tccagtctaa acatttact attaccccct ctggcaaaac     1440
ttcttttgca aaagcctctc gctattttgg tttttatcgt cgtctggtaa acgagggtta    1500
tgatagtgtt gctcttacta tgcctcgtaa ttccttttgg cgttatgtat ctgcattagt    1560
tgaatgtggt attcctaaat ctcaactgat gaatctttct acctgtaata atgttgttcc    1620
gttagttcgt tttattaacg tagattttc ttcccaacgt cctgactggt ataatgagcc     1680
agttcttaaa atcgcataag gtaattcaca atgattaaag ttgaaattaa accatctcaa    1740
gcccaattta ctactcgttc tggtgtttct cgtcagggca agccttattc actgaatgag    1800
cagctttgtt acgttgattt gggtaatgaa tatccggttc ttgtcaagat tactcttgat    1860
gaaggtcagc cagcctatgc gcctggtctg tacaccgttc atctgtcctc tttcaaagtt    1920
ggtcagttcg gttcccttat gattgaccgt ctgcgcctcg ttccggctaa gtaacatgga    1980
gcaggtcgcg gatttcgaca caatttatca ggcgatgata caaatctccg ttgtactttg    2040
tttcgcgctt ggtataatcg ctgggggtca agatgagtg tttagtgta ttctttcgcc      2100 tctttcgttt taggttggtg ccttcgtagt ggcattacgt attttacccg tttaatggaa    2160
acttcctcat gaaaaagtct ttagtcctca aagcctctgt agccgttgct accctcgttc    2220
cgatgctgtc tttcgctgct gagggtgacg atcccgcaaa agcggccttt aactccctgc    2280
aagcctcagc gaccgaatat atcggttatg cgtgggcgat ggttgttgtc attgtcggcg    2340
caactatcgg tatcaagctg tttaagaaat tcacctcgaa agcaagctga taaaccgata    2400
caattaaagg ctccttttgg agcctttttt tttggagatt tcaacgtga aaaaattatt     2460 attcgcaatt cctttagttg ttcctttcta ttctcactcc gctgaaactg ttgaaagttg    2520
tttagcaaaa cccatacag aaaattcatt tactaacgtc tggaaagacg acaaaacttt     2580
agatcgttac gctaactatg agggttgtct gtggaatgct acaggcgttg tagtttgtac    2640
tggtgacgaa actcagtgtt acggtacatg gttcctatt gggcttgcta tccctgaaaa     2700
tgagggtggt ggctctgagg gtggcggttc tgagggtggc ggttctgagg gtggcggtac    2760
taaacctcct gagtacggtg atacacctat tccgggctat acttatatca accctctcga    2820
cggcacttat ccgcctggta ctgagcaaaa ccccgctaat cctaatcctt tcttgagga    2880 gtctcagcct cttaatactt tcatgtttca gaataatagg ttccgaaata ggcaggggc     2940 attaactgtt tatacgggca ctgttactca aggcactgac cccgttaaaa cttattacca    3000
gtacactcct gtatcatcaa aagccatgta tgacgcttac tggaacggta aattcagaga    3060
ctgcgctttc cattctggct ttaatgaaga tccattcgtt tgtgaatatc aaggccaatc    3120
gtctgacctg cctcaacctc ctgtcaatgc tggcggcggc tctggtggtg gttctggtgg    3180
cggctctgag ggtggtggct ctgagggtgg cggttctgag ggtggcggct ctgagggagg    3240
cggttccggt ggtggctctg gttccggtga ttttgattat gaaaagatgg caaacgctaa    3300
taagggggct atgaccgaaa atgccgatga aaacgcgcta cagtctgacg ctaaaggcaa    3360
acttgattct gtcgctactg attacggtgc tgctatcgat ggtttcattg gtgacgtttc    3420
cggccttgct aatggtaatg gtgctactgg tgattttgct ggctctaatt cccaaatggc    3480
tcaagtcggt gacggtgata attcaccttt aatgaataat ttccgtcaat atttaccttc    3540
cctccctcaa tcggttgaat gtcgcccttt tgtctttagc gctggtaaac catatgaatt    3600
ttctattgat tgtgacaaaa taaacttatt ccgtggtgtc tttgcgtttc ttttatatgt    3660
```

```
tgccaccttt atgtatgtat tttctacgtt tgctaacata ctgcgtaata aggagtctta    3720
atcatgccag ttcttttggg tattccgtta ttattgcgtt tcctcggttt ccttctggta    3780
actttgttcg gctatctgct tactttcttt aaaaagggct tcggtaagat agctattgct    3840
atttcattgt ttcttgctct tattattggg cttaactcaa ttcttgtggg ttatctctct    3900
gatattagcg ctcaattacc ctctgacttt gttcaggtg  ttcagttaat tctcccgtct    3960
aatgcgcttc cctgttttta tgttattctc tctgtaaagg ctgctatttt cattttgac    4020 gttaaacaaa aaatcgtttc ttatttggat tgggataaat aatatggctg tttattttgt    4080
aactggcaaa ttaggctctg gaaagacgct cgttagcgtt ggtaagattc aggataaaat    4140
tgtagctggg tgcaaaatag caactaatct tgatttaagg cttcaaaacc tcccgcaagt    4200
cgggaggttc gctaaaacgc ctcgcgttct tagaataccg ataagccttc tatatctga    4260 tttgcttgct attgggcgcg gtaatgattc ctacgatgaa aataaaaacg gcttgcttgt    4320
tctcgatgag tgcggtactt ggtttaatac ccgttcttgg aatgataagg aaagacagcc    4380
gattattgat tggtttctac atgctcgtaa attaggatgg gatattattt ttcttgttca    4440
ggacttatct attgttgata aacacgcgcg ttctgcatta gctgaacatg ttgtttattg    4500
tcgtcgtctg gacagaatta ctttaccttt tgtcggtact ttatattctc ttattactgg    4560
ctcgaaaatg cctctgccta aattacatgt tggcgttgtt aaatatggcg attctcaatt    4620
aagccctact gttgagcgtt ggctttatac tggtaagaat ttgtataacg catatgatac    4680
taaacaggct ttttctagta attatgattc cggtgtttat tcttatttaa cgccttattt    4740
atcacacggt cggtatttca aaccattaaa tttaggtcag aagatgaaat taactaaaat    4800
atatttgaaa aagttttctc gcgttctttg tcttgcgatt ggatttgcat cagcatttac    4860
atatagttat ataacccaac ctaagccgga ggttaaaaag gtagtctctc agacctatga    4920
ttttgataaa ttcactattg actcttctca gcgtcttaat ctaagctatc gctatgtttt    4980
caaggattct aagggaaaat taattaatag cgacgattta cagaagcaag gttattcact    5040
cacatatatt gatttatgta ctgtttccat taaaaaaggt aattcaaatg aaattgttaa    5100
atgtaattaa ttttgttttc ttgatgtttg tttcatcatc ttcttttgct caggtaattg    5160
aaatgaataa ttcgcctctg cgcgattttg taacttggta ttcaaagcaa tcaggcgaat    5220
ccgttattgt ttctcccgat gtaaaaggta ctgttactgt atattcatct gacgttaaac    5280
ctgaaaatct acgcaatttc tttatttctg ttttacgtgc aataattttt gatatggttg    5340
gttcasttcc ttccataatt cagaagtata atccaaacaa tcaggattat attgatgaat    5400
tgccatcatc tgataatcag gaatatgatg ataattccgc tccttctggt ggtttctttg    5460
ttccgcaaaa tgataatgtt actcaaactt ttaaaattaa taacgttcgg gcaaaggatt    5520
taatacgagt tgtcgaattg tttgtaaagt ctaatacttc taaatcctca aatgtattat    5580
ctattgacgg ctctaatcta ttagttgtta gtgcacctaa agatatttta gataaccttc    5640
ctcaattcct ttcactgtt  gatttgccaa ctgaccagat attgattgag gtttgatat    5700 ttgaggttca gcaaggtgat gctttagatt tttcatttgc tgctggctct cagcgtggca    5760
ctgttgcagg cggtgttaat actgaccgcc tcacctctgt tttatcttct gctggtggtt    5820
cgttcggtat ttttaatggc gatgttttag ggctatcagt tcgcgcatta aagactaata    5880
gccattcaaa aatattgtct gtgccacgta ttcttacgct ttcaggtcag aagggttcta    5940
tctctgttgg ccagaatgtc ccttttatta ctggtcgtgt gactggtgaa tctgccaatg    6000
```

-continued

```
taaataatcc atttcagacg attgagcgtc aaaatgtagg tatttccatg agcgttttc    6060 ctgttgcaat ggctggcggt aatattgttc tggatattac cagcaaggcc gatagtttga   6120
gttcttctac tcaggcaagt gatgttatta ctaatcaaag aagtattgct acaacggtta   6180
atttgcgtga tggacagact cttttactcg gtggcctcac tgattataaa aacacttctc   6240
aagattctgg cgtaccgttc ctgtctaaaa tccctttaat cggcctcctg tttagctccc   6300
gctctgattc caacgaggaa agcacgttat acgtgctcgt caaagcaacc atagtacgcg   6360
ccctgtagcg gcgcattaag cgcggcgggt gtggtggtta cgcgcagcgt gaccgctaca   6420
cttgccagcg ccctagcgcc cgctcctttc gctttcttcc cttcctttct cgccacgttc   6480
gccggctttc cccgtcaagc tctaaatcgg ggctccctt tagggttccg atttagtgct    6540
ttacggcacc tcgaccccaa aaaacttgat ttgggtgatg gttcacgtag tgggccatcg   6600
ccctgataga cggttttttcg cccttttgacg ttggagtcca cgttctttaa tagtggactc  6660
ttgttccaaa ctggaacaac actcaaccct atctcgggct attcttttga tttataaggg   6720
attttgccga tttcggaacc accatcaaac aggattttcg cctgctgggg caaaccagcg   6780
tggaccgctt gctgcaactc tctcagggcc aggcggtgaa gggcaatcag ctgttgcccg   6840
tctcgctggt gaaagaaaaa accaccctgg cgcccaatac gcaaaccgcc tctccccgcg   6900
cgttggccga ttcattaatg cagctggcac gacaggtttc ccgactggaa agcgggcagt   6960
gagcgcaacg caattaatgt gagttagctc actcattagg caccccaggc tttacacttt   7020
atgcttccgg ctcgtatgtt gtgtggaatt gtgagcggat aacaatttca cacaggaaac   7080
agc                                                                  7083
```

<210> SEQ ID NO 2
<211> LENGTH: 2321
<212> TYPE: DNA
<213> ORGANISM: Artificial Sequence
<220> FEATURE:
<223> OTHER INFORMATION: Description of Artificial Sequence: pORFES II

<400> SEQUENCE: 2

```
gaattctgaa gcctgctttt ttatactaac ttgagcgtct agagttaata acaaggagac     60
agtatcgatg aaaaagacag ctatcgcgat tgcagtggca ctggctggtt tcgctagcgt    120
agctcaggcc ggccaagctt ccctggtcac cgtcagcagt ggtggcggac acccagaaac   180
gctggtgaaa gtaaaagatg ctgaagatca gttgggtgca cgagtgggtt acatcgaact   240
ggatctcaac agcggtaaga tccttgagag ttttcgcccc gaagaacgtt ttccaatgat   300
gagcactttt aaagttctgc tatgtggcgc ggtattatcc cgtattgacg ccgggcaaga   360
gcaactcggt cgccgcatac actattctca gaatgacttg gttgagtact caccagtcac   420
agaaaagcat cttacggatg gcatgacagt aagagaatta tgcagtgctg ccataaccat   480
gagtgataac actgcggcca acttacttct gacaacgatc ggaggaccga aggagctaac   540
cgcttttttg cacaatatgg gggatcatgt aactcgcctt gatcgttggg aaccggagct   600
gaatgaagcc ataccaaacg acgagcgtga caccacgatg cctgcagcaa tggcaacaac   660
gttgcgcaaa ctattaactg gcgaactact tactctagct tcccggcaac aattaataga   720
ctggatggag gcggataaag ttgcaggacc acttctgcgc tcggcccttc cggctggctg   780
gtttattgct gataaatctg gagccggtga gcgtgggtct cgcggtatca ttgcagcact   840
ggggccagat ggtaagccct cccgtatcgt agttatctac acgacgggga gtcaggcaac   900
tatggatgaa cgaaatagac agatcgctga gataggtgcc tcactgatta agcattggta   960
```

```
agtcgactaa taaagcccgc ctaatcagcg ggcttttttt tctcgggccg cgttgctggc    1020 gttttttccat aggctccgcc ccctgacga gcatcacaaa aatcgacgct caagtcagag    1080
gtggcgaaac ccgacaggac tataaagata ccaggcgttt cccctggaa gctccctcgt     1140 gcgctctcct gttccgaccc tgccgcttac cggatacctg tccgcctttc tcccttcggg    1200
aagcgtggcg ctttctcata gctcacgctg taggtatctc agttcggtgt aggtcgttcg    1260
ctccaagctg ggctgtgtgc acgaaccccc cgttcagccc gaccgctgcg ccttatccgg    1320
taactatcgt cttgagtcca acccggtaag acacgactta tcgccactgg cagcagccac    1380
tggtaacagg attagcagag cgaggtatgt aggcggtgct acagagttct gaagtggtg     1440 gcctaactac ggctacacta aaggacagt atttggtatc tgcgctctgc tgaagccagt     1500
taccttcgga aaagagttg gtagctcttg atccggcaaa caaaccaccg ctggtagcgg     1560 tggtttttttt gtttgcaagc agcagattac gcgcagaaaa aaggatctc aactgttaca    1620 caactcttgt agccgattaa taaagcgtgc aacatggaag ccatcacaaa ctgcatgatg    1680
aacctgtact gagagcggca ataacagtct atccccttct tgctgatatt ttgccattgt    1740
tataatgggt gcaaaataat cggtaaaatt agcaacattt aaattaaagc tatcaaaatt    1800
aacccaaggt aatgctgaaa tatttaaatg attttctggt gttacccctt gaggaaataa    1860
cttggtatca cttttataac gttccattac cgataaataa ttcaccataa attgatcaat    1920
atcggatgag tatgggcaac tcagtgctga aaatgtctct gtttcttgat ggaatacggt    1980
gaattgtgga tcaactgaat cccatacgat caattcatca tcttttatcg ccattctcaa    2040
ctcatcaaat tgattcacgg cctgagcaat cagatagatc attaccggat aaaacttata    2100
cgctgaatca tccaatgact tttttaacgt cgtgatatca attttgcttg ttaagctaaa    2160
accacatggt aaacgatgcc gataaaactc aaaatgctca cggcgaaccc aatttttac    2220 atcaaatttt gtatagttca taatcgatcc cttctgaatt tttatttact aagaacctat    2280
cccaaaagga tttattcca gacaatgatg cacaggcaag a                         2321
```

<210> SEQ ID NO 3
<211> LENGTH: 2337
<212> TYPE: DNA
<213> ORGANISM: Artificial Sequence
<220> FEATURE:
<223> OTHER INFORMATION: Description of Artificial Sequence: pORFES IV

<400> SEQUENCE: 3

```
gaattctgaa gcctgctttt ttatactaac ttgagcgtct agagttaata caaggagac      60 agtatcgatg aaaaagacag ctatcgcgat tgcagtggca ctggctggtt tcgctagcgt    120
agctcaggcc ggctggtggc ggtggctccc aagcttccct ggtcaccgtc agcagtggtg    180
gcggacaccc agaaacgctg gtgaaagtaa agatgctga agatcagttg ggtgcacgag    240
tgggttacat cgaactggat ctcaacagcg gtaagatcct tgagagtttt cgccccgaag    300
aacgttttcc aatgatgagc acttttaaag ttctgctatg tggcgcggta ttatcccgta    360
ttgacgccgg gcaagagcaa ctcggtcgcc gcatacacta ttctcagaat gacttggttg    420
agtactcacc agtcacagaa aagcatctta cggatggcat gacagtaaga gaattatgca    480
gtgctgccat aaccatgagt gataacactg cggccaactt acttctgaca acgatcggag    540
gaccgaagga gctaaccgct ttttgcaca atatgggggga tcatgtaact cgccttgatc    600
gttgggaacc ggagctgaat gaagccatac caaacgacga gcgtgacacc acgatgcctg    660
```

-continued

```
cagcaatggc aacaacgttg cgcaaactat taactggcga actacttact ctagcttccc    720
ggcaacaatt aatagactgg atggaggcgg ataaagttgc aggaccactt ctgcgctcgg    780
cccttccggc tggctggttt attgctgata aatctggagc cggtgagcgt gggtctcgcg    840
gtatcattgc agcactgggg ccagatggta agccctcccg tatcgtagtt atctacacga    900
cggggagtca ggcaactatg gatgaacgaa atagacagat cgctgagata ggtgcctcac    960
tgattaagca ttggtaagtc gactaataaa gcccgcctaa tcagcgggct tttttttctc   1020
gggccgcgtt gctggcgttt ttccataggc tccgcccccc tgacgagcat cacaaaaatc   1080
gacgctcaag tcagaggtgg cgaaacccga caggactata aagataccag gcgtttcccc   1140
ctggaagctc cctcgtgcgc tctcctgttc cgaccctgcc gcttaccgga tacctgtccg   1200
cctttctccc ttcgggaagc gtggcgcttt ctcatagctc acgctgtagg tatctcagtt   1260
cggtgtaggt cgttcgctcc aagctgggct gtgtgcacga acccccgtt cagcccgacc    1320 gctgcgcctt atccggtaac tatcgtcttg agtccaaccc ggtaagacac gacttatcgc   1380
cactggcagc agccactggt aacaggatta gcagagcgag gtatgtaggc ggtgctacag   1440
agttcttgaa gtggtggcct aactacggct acactagaag gacagtattt ggtatctgcg   1500
ctctgctgaa gccagttacc ttcggaaaaa gagttggtag ctcttgatcc ggcaaacaaa   1560
ccaccgctgg tagcggtggt ttttttgttt gcaagcagca gattacgcgc agaaaaaaag   1620
gatctcaact gttacacaac tcttgtagcc gattaataaa gcgtgcaaca tggaagccat   1680
cacaaactgc atgatgaacc tgtactgaga gcggcaataa cagtctatcc ccttcttgct   1740
gatattttgc cattgttata atgggtgcaa aataatcggt aaaattagca acatttaaat   1800
taaagctatc aaaattaacc caaggtaatg ctgaaatatt taaatgattt tctggtgtta   1860 cccccttgagg aaataacttg gtatcacttt tataacgttc cattaccgat aaataattca   1920
ccataaattg atcaatatcg gatgagtatg ggcaactcag tgctgaaaat gtctctgttt   1980
cttgatggaa tacggtgaat tgtggatcaa ctgaatccca tacgatcaat tcatcatctt   2040
ttatcgccat tctcaactca tcaaattgat tcacggcctg agcaatcaga tagatcatta   2100
ccggataaaa cttatacgct gaatcatcca atgactttt taacgtcgtg atatcaattt    2160
tgcttgttaa gctaaaacca catggtaaac gatgccgata aaactcaaaa tgctcacggc   2220
gaacccaatt ttttacatca aattttgtat agttcataat cgatcccttc tgaattttta   2280
tttactaaga acctatccca aaaggatttt attccagaca atgatgcaca ggcaaga     2337
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: DB3BLAB
      primer

<400> SEQUENCE: 4

```
tctagaagct tgcccaccct cattcctgtt gaagct                              36
```

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: JC102
      primer

<400> SEQUENCE: 5

```
ggcgctgcta gcgtagctca ggctcaggtg aaactgctcg ag          42

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: M13-JC117
      primer

<400> SEQUENCE: 6
tcatcatact agtgatggcg ttcctattgg t                      31

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: M13-JC118
      primer

<400> SEQUENCE: 7
aagcttatga tgtctagagc tgtttcctgt gtgaa                  35

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:
      SYNVIII-JC119 primer

<400> SEQUENCE: 8
taagcttctg gcgccgtccc tgcagaaggt ga                     32

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      SYNVIII-JC120 primer

<400> SEQUENCE: 9
aagctagctt aaaaaaaagc ccgc                              24

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: DB3 R100
      primer

<400> SEQUENCE: 10
gaagtaacgg ttgac                                        15

<210> SEQ ID NO 11
<211> LENGTH: 15
<212> TYPE: DNA
<213> ORGANISM: Artificial Sequence
```

-continued

```
<220> FEATURE:
<223> OTHER INFORMATION: Description of Artificial Sequence:  DB3 W100
      primer

<400> SEQUENCE: 11
gaagtaccag ttgac                                                        15
```

MODULATION OF POLYPEPTIDE DISPLAY ON MODIFIED FILAMENTOUS PHAGE

CROSS REFERENCE TO RELATED APPLICATIONS

This application is a continuation-in-part of U.S. Provisional Patent Application No. 60/096,326, filed Aug. 12, 1998, the entire disclosure of which is incorporated herein by reference.

Funds used to support some of the studies reported herein were provided by the United States Government (Department of the Army ARL No DAAL03-92-G-0215). The United States Government may, therefore, have certain rights in the invention disclosed herein.

TECHNICAL FIELD OF THE INVENTION

The field of this invention is phage display of polypeptides. More particularly, this invention relates to a modified filamentous phage that allows for displaying polypeptides on the surface in a range of densities.

BACKGROUND OF THE INVENTION

Phage display of antibodies was initially based on systems developed for the display of peptides (Smith, *Science* 228, 1315–7, 1985). Antibody single chain variable domains were fused to the coat protein gene (gpIII), (McCafferty, et al., *Nature* 348, 552–554, 1990) resulting in all the gpIII molecules displaying fusion antibodies. However, the fusion of a polypeptide to the gpIII reduced the ability of the phage to infect bacteria and secondly the multivalent display at the tip of the phage resulted in avidity selection rather than affinity discrimination. Utilizing a phagemid vector (to present the gpIII-fusion) and helper phage rescue (to introduce the wild type gpIII), the valency of fusion display was reduced and infectivity restored (Bass, et al, *Proteins: Structure, Function, and Genetics* 8, 309–314, 1990). Likewise, the display of heterodimeric polypeptides such as antibody F(ab) fragments as either major (gpVIII) (Kang, et al., *Proc. Natl Acad. Sci. USA* 88, 4363–66, 1991), or minor (gpIII) (Barbas, et al., *Proc. Natl. Acad. Sci. USA* 88, 7978–82, 1991; Garrard, et al., *Bio/Technol.* 9, 1373–77, 1991) coat protein fusions has successfully utilized phagemid with helper phage rescue.

Phage display of antibody fragments and other polypeptides has gained acceptance as a useful tool in contemporary molecular immunology. The density of polypeptide display per filamentous phage particle is influenced by the choice of which phage coat protein is used as fusion partner and the type of vector system used. Molecules expressed from nucleotide sequences fused with the sole copy of gpIII on the phage genome such as fd or M13 resulted in a multivalent cluster display (tri-penta valent) and reduced infectivity of bacteria (McCafferty et al., *Nature* 348, 552–554, 1990; Smith, *Science* 228, 1315–7, 1985). Multivalent binding of phage with ligand would favor avidity selection and limit the ability to discriminate between modest gains in affinity (Cwirla, et al., *Proc. Natl Acad. Sci. USA* 87, 6378–82., 1990). This may be desirable when attempting to isolate ligand binding molecules of lower affinity. Phagemid vectors encoding phage coat protein fusion polypeptides used in conjunction with helper phage rescue, generated phage with restored infectivity and reduced valency permitting enrichment for high affinity interactions (Bass, S., et al. *Proteins: Structure, Function, and Genetics* 8, 309–314, 1990).

Both the high and low density display systems have uses in accessing ligands against target receptors or tissues. It would be desirable to create a phage display system in which the density of the displayed fusion moieties on the phage particle could be modulated from a few displayed copies to less than 1 per phage. To achieve this with existing vectors requires shuttling of inserts between gpIII phage and gpVIII/gpIII phagemid vectors. However this may also be attained by utilizing a single M13 phage based vector with a synthetic second copy of the gene encoding gpIII or gpVIII (i.e. pseudo wild type) as a fusion partner (Huse, et al., *J. Immunol.* 149, 3914–20, 1992), and manipulating the phage growth conditions to favor low or moderate rates of fusion incorporation into the phage filament. Incorporating the display expression cassette onto the phage genome may also have the added benefits of fusion expression being synchronous with phage morphogenesis. The present invention describe a phage vector in which a polypeptide is displayed on the phage surface. This display system was used to investigate the modulation of display fusion on phage resulting in optimal phage display as determined by relative panning enrichment efficacy.

BRIEF SUMMARY OF THE INVENTION

The present invention discloses a phage vector for the display of polypeptides on the surface of a modified filamentous phage which permits facile manipulation of the valency of display. The gene encoding the polypeptide is fused to a synthetic copy of a major coat protein gene which permits incorporation into the phage during assembly of the filament.

Thus, in one aspect, the present invention provides a modified filamentous phage expression vector. That vector includes a gene encoding a wild type major coat protein of the phage; a leaky, inducible promoter; a gene encoding a synthetic major coat protein of the phage; and a directional cloning site for receiving a nucleotide insert. The insert is a nucleotide that includes a sequence that encodes a translation initiation site, contains a leader sequence that directs polypeptide expression to a bacterial periplasmic membrane and a polypeptide encoding sequence. The directional cloning site is situated between the promoter and the gene encoding the synthetic major coat protein of the phage, such that the polypeptide is expressed as a fusion protein with the synthetic major coat protein.

In preferred embodiments, the translation initiation site is a ribosome binding site, the promotor is the lac promoter, the leader sequence is ompA, the wild type major coat protein of the phage is gpVIII, the synthetic major coat protein of the phage is a synthetic gpVIII, and the polypeptide is a ligand-binding heterodimeric antibody. An especially preferred filamentous phage is M13. A preferred modified M13 vector of this invention is designated herein as JC-M13-88.

Preferably, the nucleotide insert of the modified filamentous phage is obtained from a pre-selection open reading frame expression and secretion plasmid (pORFES), preferably pORFES II or pORFES IV.

In a related aspect, the present invention provides a process for expressing a polypeptide. The process includes the steps of (a) inserting a nucleotide sequence containing a translation initiation site encoding region, a leader sequence that targets expression of a polypeptide to a bacterial periplasmic membrane and a polypeptide coding sequence that into a directional cloning site of a filamentous phage that contains a gene encoding a wild type phage major coat protein, an inducible promoter and a gene that encodes a synthetic phage major coat protein wherein the directional cloning site is located between the inducible promoter and the gene encoding the synthetic phage major coat protein; and (b) propagating the filamentous phage from step (a) in a bacterium. Preferred translation initiation sites, promoters, leader sequences, polypeptides and major coat proteins are the same as set forth above. A preferred directional cloning site comprises a pair of restriction enzyme sites. Exemplary such enzyme sites are XbaI and HindIII.

The density of the polypeptides displayed on phage may be modulated by phage altering growth conditions. Propagation is preferably carried out at a temperature of from about 25° C. to about 37° C. in the absence or presence of inducers that induce expression by way of the inducible promoter. Lowering the temperature of phage propagation reduced the overall phage yield, yet increased the quality of the antibody display. Likewise the addition of inducers during phage propagation reduced the phage yield but led to enhanced the recovery of phage during panning.

BRIEF DESCRIPTION OF THE DRAWINGS

In the drawings that form a portion of the specification.

FIGS. 4-1, 4-2 and 4-3 show the nucleotide sequence (SEQ ID NO:1) of a modified filamentous phage of this invention.

FIGS. 5-1 and 5-2 show the nucleotide sequence (SEQ ID NO:2) of pORFES II.

FIG. 6 shows the nucleotide sequence (SEQ ID NO:3) of pORFES IV.

DETAILED DESCRIPTION OF THE INVENTION

I. The Invention

Figure 1:
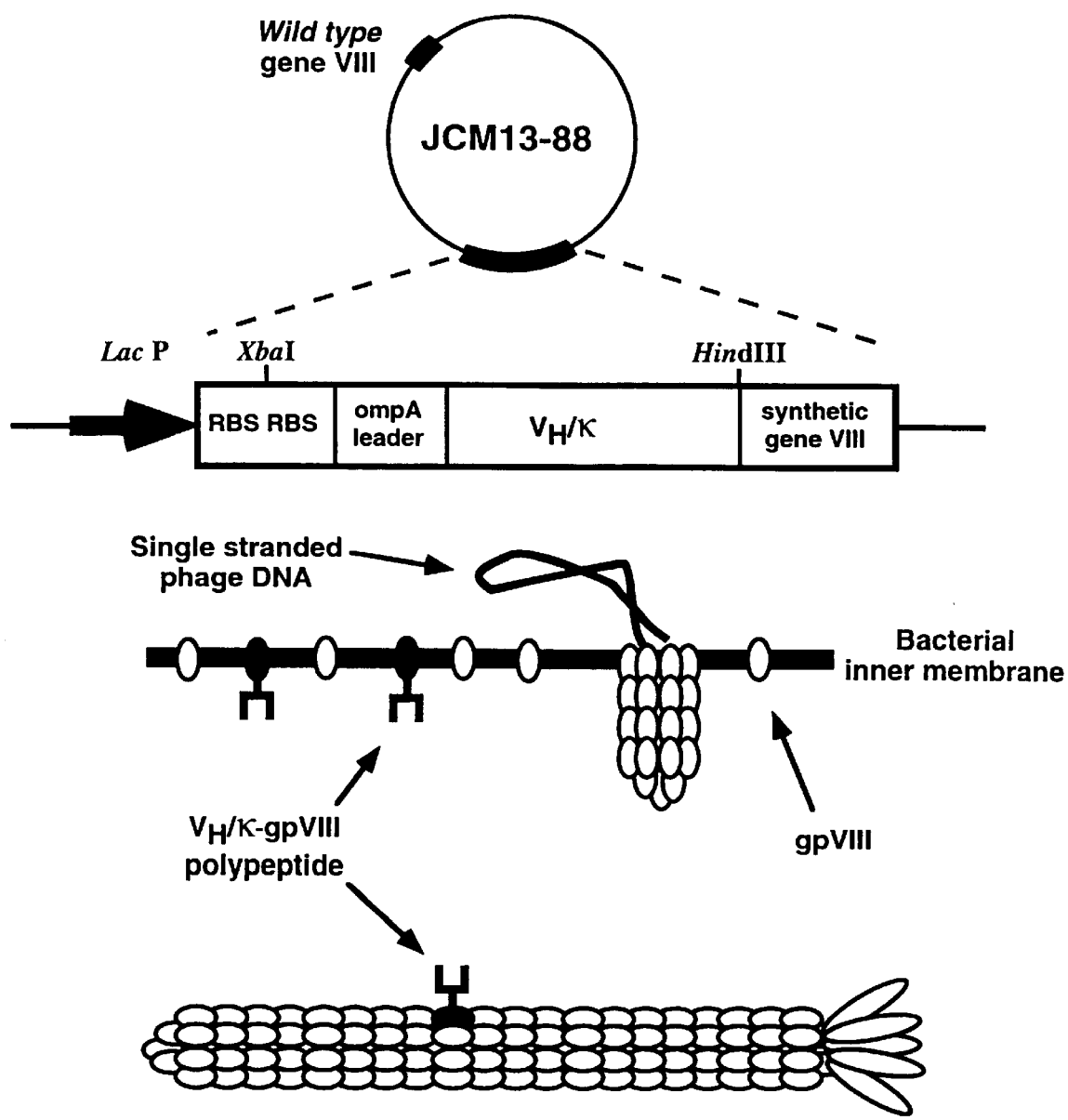
FIG. 1 shows a schematic illustration of JC-M13-88 phage display system. The $V_H/\kappa$ is inserted into the JC-M13-88 vector from pORFES as an XbaI-HindIII fragment. The $V_H/\kappa$ molecule is expressed as a fusion with the product of a synthetic gpVIII gene, which is not homologous with the wild-type gene present in the phage genome. Expression from dual ribosome binding sites (RBS) is controlled by the Lac promoter and the $V_H/\kappa$-gpVIII fusion molecule is targeted for secretion through the bacterial membrane by the ompA leader sequence. The single stranded phage DNA is encapsulated by the wild type gpVIII and one or more $V_H/\kappa$-gpVIII fusion molecules may also be incorporated into the phage protein coat.

This invention provides a modified filamentous phage and methods for using that phage to express and display polypeptides on its surface at varying density.

II. Modified Filamentous Phage

As is well known in the art, a filamentous bacteriophage, hereinafter a filamentous phage, is a member of a group of related viruses that infect bacteria. The term filamentous refers to the long, thin particles of an elongated capsule that envelope deoxyribonucleic acid (DNA) (the phage genome). Well known filamentous phage include fd, f1 and M13. Mature capsules of filamentous phage contain five encoded gene products known as coat proteins: gpVIII, gpIII, gpIV, gpVII and gpIX.

A modified filamentous phage of the present invention comprises a gene encoding a wild type phage coat protein and a gene encoding a synthetic form of a coat protein. In a preferred embodiment, the phage contains a gene that encodes a wild type coat protein and a gene that encodes a synthetic form of that same coat protein. In an especially preferred embodiment, the coat protein is major coat protein gpVIII.

The modified phage also contains an inducible promoter. Inducible promoters are well known in the art. An especially preferred such well known inducible promoter is the lac promoter. Situated between the promoter and the gene for the synthetic coat protein is a directional cloning site designed for receiving a nucleotide insert. As used herein the phrase "directional cloning site" indicates an insertion site that orients the insert such that expression of a polypeptide coding sequence in the insert will be under the control of the promoter and the polypeptide will be expressed as a fusion protein with the synthetic coat protein. A preferred directional cloning site is a pair of restriction enzyme sites that are the same as restriction enzyme sites at the ends of the nulceotide insert. An exemplary and preferred such restricition enzyme site pair is XbaI and HindIII.

The nucleotide insert to be received by the modified phage comprises a translation initiation site, a leader sequence and a polypeptide coding region. Translation initiation sites are well known in the art. An exemplary and preferred such initiation site is a ribosome binding site. Ribosome binding sites for use in filamentous phage are well known in the art (See, e.g., U.S. Pat. No. 5,658,727, the disclosure of which is incorporated herein by reference). A leader sequence is located upstream to the polypeptide coding region and acts as a signal that targets the polypeptide to the periplasmic membrane of a bacterium. Such leader, signal sequences and their use with filamentous phage are well known in the art (See. e.g., U.S. Pat. No. 5,658,727, the disclosure of which is incorporated herein by reference). An exemplary and preferred leader sequence is ompA.

In a preferred embodiment, the polypeptide is a ligand-binding heterodimeric receptor. Preferred heterodimeric receptors include immunoglobulins, major histocompatibility antigens of class I or II, lymphocyte receptors, integrins and the like heterodimeric receptors. Immunoglobulins (antibody molecules) can be in the form of Fab or Fv fragments, or other portions of an antibody molecule that contain regions of the variable domain of the heavy and light chains.

Preferably the receptor produced by the subject invention is heterodimeric and is therefore normally comprised of two different polypeptide chains, which together assume a conformation having a binding affinity, or association constant for the preselected ligand that is different, preferably higher, than the affinity or association constant of either of the polypeptides alone, i.e., as monomers. The heterodimeric receptor is referred to as a ligand-binding heterodimeric receptor to connote its ability to bind ligand.

One or both of the different polypeptide chains is preferably derived from the variable region of the light and heavy chains of immunoglobulin. Typically, polypeptides comprising the light ($V_L$) and heavy ($V_H$) variable regions are employed together for binding a preselected ligand.

Figure 2:
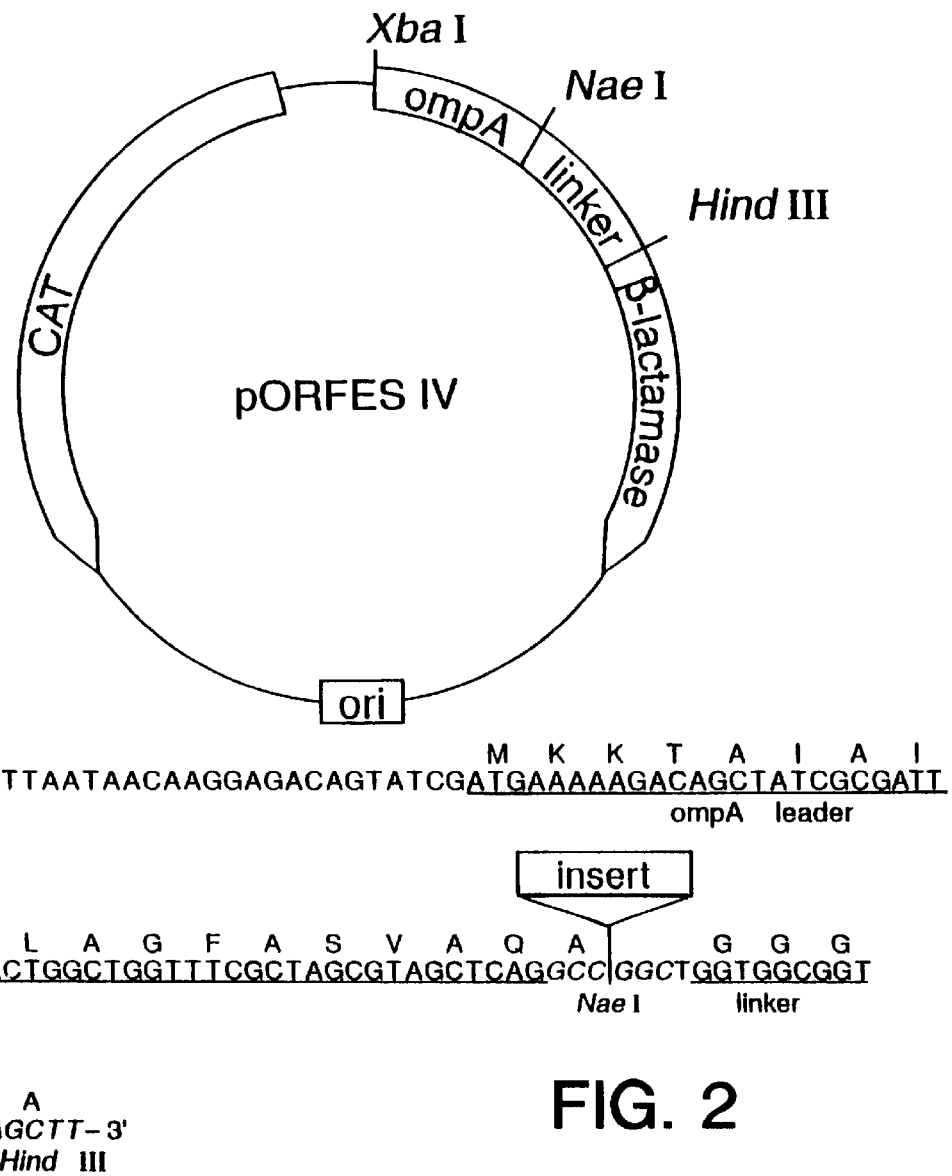
FIG. 2 shows a schematic drawing of a pre-selection open reading frame expression and secretion plasmid (pORFESIV) and a partial nucleotide sequence of that plasmid.
Figure 3:
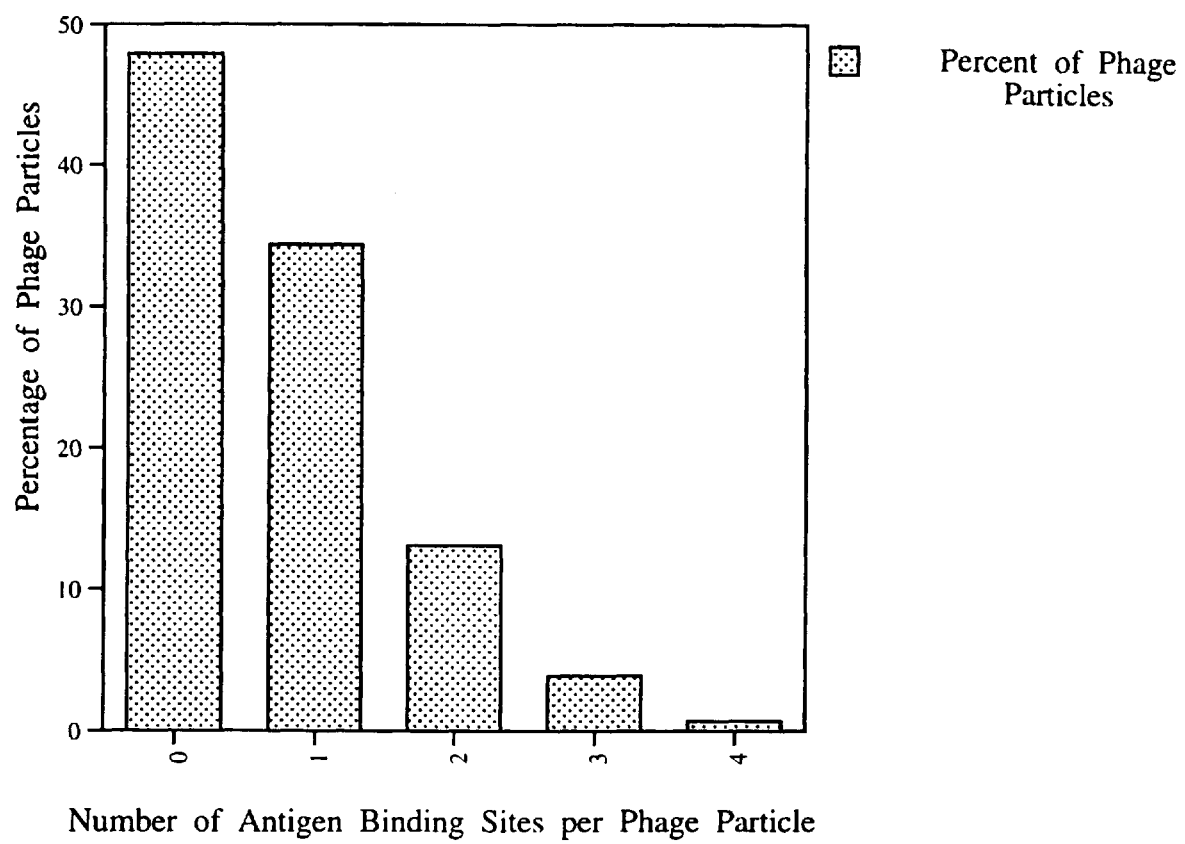
FIG. 3 shows an analysis of $V_H/k$-gpVIII incorporation into phage filament using electron microscopy. DB3 R100 antibody phage were grown at 25C in the presence of IPTG. Phage were applied to grids and probed with PHS-BSA gold conjugates. The distribution of gold particles per phage was determined by visual examination of phage particles.

A nucleotide insert for use with a modified phage of this invention can be prepared using any means known in the art. In a preferred embodiment, the insert is obtained from an open reading frame expression secretion vector designated herein as pORFES. A schematic illustration of one pORFES (pORFES IV) is shown in FIG. 2. Nucleotide sequences of preferred pORFES are shown in FIG. 5 (pORFES II, SEQ ID NO:2) and FIG. 6 (pORFES IV, SEQ ID NO:3).

As shown in FIG. 2, pORFES IV contains the β-lactamase gene preceded by the ompA leader sequence (underlined) with a 4×gly 1×ser linker (underlined). An additional base between the leader and the linker results in a frame shift of the β-lactamase. A NaeI site between the leader sequence and the linker allows subcloning of blunt ended DNA. The CAT gene in the vector backbone permits the vector propagation using chloramphenicol if the vector does not contain an insert restoring the frame of the β-lactamase. Only the ligation of inserts restoring the frame of the β-lactamase which do not contain a stop codon should result in carbenicillin resistance. The XbaI/HindIII cloning sites permit cloning into compatible sites of a modified phage display vector such as JC-M13-88.

Gel-purified polypeptide coding sequences are digested with 70 ng DNAse containing $MnCl_2$ and the reaction terminated by adding EDTA. After precipitation, the fragments are treated with mung bean nuclease. The resulting mixture containing blunt ended fragments is ligated into restriction enzyme digested pORFES between the ompA leader sequence and the β-lactamase gene. Only the inserts which restore the correct open reading frame and are readily translocated into the periplasm along with the fused β-lactamase confer β-lactam antibiotic resistance. The ligation products are transfected into non-suppressing *E. coli* via electroporation and propagated overnight in Super Broth containing 100 μg/ml carbenicillin at 37° C. The transfection efficiency is monitored by plating aliquots on agar plates containing chloramphenicol with or without 100 carbenicillin. The pORFES library DNA is recovered from the overnight culture and inserts released by digestion with XbaI and HindIII.

A preferred modified filamentous phage of this invention is designated herein as JC-M13-88. A schematic illustration of this phage is shown in FIG. 1 and the nucleotide sequence (SEQ ID NO:1) of this phage is shown in FIG. 4.

The present invention further provides a kit for the expression of a polypeptide. The kit comprises a modified filamentous phage of this invention together with instructions for use of that phage. The kit can further include solvents and reagents for the use of that phage. A preferred phage for inclusion in the kit is the same as set forth above.

III. Uses of Modified Filamentous Phage

In a related aspect, the present invention provides a process for expressing a polypeptide. The polypeptide is expressed on the surface of a modified filamentous phage as set forth above. The polypeptide is expressed as a fusion protein with a synthetic form of a major coat protein of the phage. Suitable such coat proteins are disclosed above.

The process includes the step of inserting a nucleotide sequence containing a ribosome binding site encoding region, a leader sequence that targets expression of a polypeptide to a bacterial periplasmic membrane and a polypeptide coding sequence that into a directional cloning site of a filamentous phage that contains a gene encoding a wild type phage major coat protein, an inducible promoter and a gene that encodes a synthetic phage major coat protein. The directional cloning site is located between the inducible promoter and the gene encoding the synthetic phage major coat protein. The process further includes the step of propagating the filamentous phage in a bacterium. Preferred promoters, leader sequences, polypeptides and major coat proteins are the same as set forth above. A preferred directional cloning site comprises a pair of restriction enzyme sites. Exemplary such enzyme sites are XbaI and HindIII. A detailed description of expressing an antibody polypeptide in accordance with the present process can be found hereinafter in the Examples.

The density of the polypeptides displayed on phage using a process of this invention can be modulated by altering growth conditions. Propagation is preferably carried out at a temperature of from about 25° C. to about 37° C. in the absence or presence of inducers that induce expression by way of the inducible promoter. Lowering the temperature of phage propagation reduced the overall phage yield, yet increased the quality of the antibody display. Likewise the addition of inducers during phage propagation reduced the phage yield but led to enhanced the recovery of phage during panning. The present process does not require the use of a helper/plasmid and has advantages over existing methods of phage display.

Using a present process, the integration of $V_H$/κ-gpVIII fusion(s) has no apparent influence on phage infectivity, and labeling studies suggested that the recombinant molecules are incorporated at a low density. Other groups have estimated the level of incorporation into the phage filament of polypeptides expressed as fusion with either gpIII or gpVIII using indirect methods (Bass, S., et al. *Proteins: Structure, Function, and Genetics* 8, 309–314, 1990; Garrard, et al., *Bio/Technol.* 9, 1373–77, 1991; Zhong,et al., *J. Biol. Chem.* 269, 24183–8, 1994). The values obtained represented the average number of coat protein fusion's within a phage population. Using electron microscopy with immunogold labeling the distribution of coat protein fusion's on phage prepared under conditions of higher density display was estimated. The maximum number of labels per JC-M13-88 phage particle was four, which is in contrast to earlier studies on phagemid pComb8/helper in which as many as 24 F(ab)-gpVIII molecules were displayed on the phage particles (Kang, A. S., et al., *Proc. Natl Acad. Sci. USA* 88, 4363–66, 1991). Using a phagemid/helper system the interval between fusion expression and helper rescue may be extended in early stages of phage preparation, thus permitting accumulation of fusion prior to phage production which permits some phage particles to take up as many as 20 copies of the fusion moiety (both helper and phagemid). In the phage only system the fusion moiety and phage morphogenesis are in concert which would preclude the incorporation of fusion approaching the extent that can be achieved with phagemids prior to helper rescue, additionally only phage displaying the fusion would encode it. One feature observed with JC-M13-88 display vector was the retention of intact inserts throughout the duration of the experiment in contrast to fusion's with gpVIII or III in phagemid vectors. In cells infected with JC-M13-88 phage the metabolic demand on infected cells is high, the addition of fusion-gpVIII molecules driven from a much weaker Lac promoter may not significantly perturb this demand, thus loss of insert expression may not confer any discernible growth advantage. However, in general it has been acknowledged that large foreign DNA inserts are often unstable in M13 based vectors (see discussion in Sam brook, et al., *Molecular Cloning: A laboratory manual*, 1989). Reducing the size of the foreign insert and of homologous nucleotide sequences within the phage genome may confer insert/phage stability. This was achieved in JC-M13-88 by replacing the Lac Z polypeptide of M13 mp18 with a non-phage leader sequence (McGuiness, et al., *Nature Biotech*. 14, 1149–54, 1996) and a synthetic second copy of the gpVIII.

Parameters influencing the yield of phage have been linked closely to conditions favoring bacterial growth. Optimal growth conditions for the bacteria should provide optimal production conditions for phage. Growth conditions during phage preparation such as temperature of phage production and induction of fusion antibody expression by IPTG were investigated. Lowering the temperature of phage propagation reduced the overall phage yield, yet increased the quality of the antibody display. Likewise the addition of IPTG during phage propagation reduced the phage yield but led to enhanced the recovery of phage during panning. The combination of lower temperature and the presence IPTG during phage propagation improved the recovery of phage in panning experiments by more than 100 fold relative to phage prepared at 37° C. in the absence of IPTG. The reduction in growth temperature and addition of IPTG may have a concerted effect on phage production and on antibody fusion assembly resulting in a higher level of display per phage particle. Enhancing the density of display in early rounds of panning may be beneficial in accessing lower affinity interactions. By adjusting the growth conditions in later panning rounds the qualitative features of the phage population may be altered to favor "lower" density display. A priori requirement for successful phage display of a polypeptide is the successful production, secretion and assembly of recombinant proteins in *E. coli* which can be influenced by a number of factors in addition to amino acid sequence (for reviews see Marston, et al, *Escherichia coli. Biochem. J*. 240, 1–12, 1986; Schein, *Bio/Technol*. 7, 1141–9, 1989). Reducing the temperature may facilitate the correct folding and assembly, and contribute to stability, of the displayed antibody. The present data show that producing a well characterized antibody phage at lower temperatures in the presence of IPTG increases the number of phage recovered in panning experiments, and increases the number of $V_H$/k-gpVIII polypeptides incorporated into the phage filament. At all growth temperatures investigated, phage produced in the presence of IPTG were more readily recovered in panning experiments than phage produced without IPTG induction. In contrast, experiments with antibody-gpVIII phage produced using a phagemid/helper phage system the opposite situation was found (Kretzschmar & Geiser, *Gene* 155, 61–65, 1995). Hence by manipulating the propagation temperature and the induction of the fusion moiety it should be possible to prepare phage for accessing based on avidity (higher density display, 25° C., +IPTG) or 2D affinity (lower density display, 37° C., −IPTG).

The present process was also evaluated for the ability to discriminate between two variants of the antibody DB3 (W100 and R100), with widely disparate affinities for PCMO-BSA yet indistinguishable affinities for PHS-BSA. The recovery of DB3 R100 over W100 on either PHS-BSA or CMO-BSA implies that R100 has a higher affinity for both ligands.

The Examples that follow illustrate preferred embodiments of the present invention and are not limiting of the specification or claims in any way.

EXAMPLE 1

Phage Construction

Alphabetical list of oligonucleotides. (restriction sites underlined),

DB3BLAB 5'-TCT AGA AGC TTG CCC ACC CTC ATT CCT GTT GAA GCT-3' (SEQ ID NO:4)

JC102 5'-GGC GCT GCT AGC GTA GCT CAG GCT CAG GTG AAA CTG CTC GAG-3' (SEQ ID NO:5)

M13-JC117 5'-TCA TCA TAC TAG TGA TGG CGT TCC TAT TGG T-3' (SEQ ID NO:6)

M13-JC118 5'-AAG CTT ATG ATG TCT AGA GCT GTT TCC TGT GTG AA-3' (SEQ ID NO:7)

SYNVIII-JC119 5'-TAA GCT TCT GGC GCC GTC CCT GCA GAA GGT GA-3' (SEQ ID NO:8)

SYNVIII-JC120 5'-AAG CTA GCT TAA AAA AAA GCC CGC-3' (SEQ ID NO:9)

Construction of modified M13. Nucleotide sequence of bacteriophage M13mpl8 (Messing, *Methods Enzymol*. 101, 20–79, 1983; Messing, *Gene* 100, 3–12, 1991; Yanisch-Peron, et al., *Gene* 33, 103–119, 1985), was amplified (94° C. for 2 min, 10 cycles; 94° C. for 30 s, 60° C. for 1 min, 68° C. for 6 min, followed by 20 cycles during which the extension time was increased by 20 s per cycle) from replicative form DNA using primers M13-JC117, M13-JC118 and the Expand™ Long Template PCR System (Boehringer Mannheim). The PCR amplified M13mp18 was treated sequentially with T4 DNA polymerase, T4 polynucleotide kinase, and finally T4 DNA ligase, using standard methods (Sam brook, et al., *Molecular Cloning: A laboratory manual*, 1989). *E. coli* XL1-Blue strain (Stratagene) were transformed with the ligated DNA and a standard M13 plaque assay was performed in the presence of IPTG and X-gal as described (Sam brook, et al., *Molecular Cloning: A laboratory manual*, 1989). Replicative form DNA was prepared from colorless plaques and the desired DNA construct identified by analyzing restriction enzyme digests. DNA coding for a pseudo gpVIII, which is not homologous to the wild-type gene but nearly identical in primary sequence, was PCR amplified (30 cycles; 94° C. for 30 s, 55° C. for 1 min, 72° C. for 1 min) from vector f88-4 ((Zhong, et al., *J. Biol. Chem*. 269, 24183–8, 1994) provided by G. P. Smith, Univ. Missouri, Mo.) using primers SynVIII-JC119 and SynVIII-JC120. The PCR product was cloned using the TA Cloning kit plasmid pCR™II (Invitrogen), and the sequence of the DNA insert was confirmed by DNA sequencing. DNA coding for the synthetic gpVIII was ligated into the modified M13. The modified phage containing the wild type and the pseudo wild type gpVIII was designated JC-M13-88.

Construction of DB3 $V_H$/k Phage. The wild type anti-progesterone antibody DB3 (He, et al., *Immunology* 84, 662–668, 1995; Wright, et al., *Nature* 295, 415–417, 1982) has a tryptophan residue at position 100 of the $V_H$ domain (designated W100). In a mutant single chain $V_H$/κ molecule position 100 is arginine (designated R100). The DNA sequences coding for the DB3 $V_H$/κ W100 (He, et al., *Immunology* 84, 662–668, 1995) and R100 variants were PCR amplified using the oligonucleotide primers JC102 and DB3BlaB and ligated into the plasmid pORFES (open reading frame/expression/secretion as Nhe—HindIII fragments, and the ligation products were transformed into bacteria. The plasmid pORFES is a low copy number plasmid in which sequences are expressed as fusions with beta lactamase. Antibiotic selection has been used to screen libraries of peptides and antibody genes fused with the bla gene for open reading frames and successful periplasmic targeting in bacteria. Here, the sub-cloning of the DB3 via pORFES was necessary both to introduce restriction enzyme sites and to provide a second ribosome binding site and the ompA leader sequence for the correct expression of the DNA insert. The 1.1 kilo base pair DNA fragments coding for the DB3 $V_H$/κ variants were excised from pORFES using XbaI and HindIII, then ligated into XbaI/HindIII treated JC-M13-88. Phage encoding and displaying the W100 and the R100 $V_H$/κ molecules were generated.

Western blotting. M13mp18 phage or DB3 R100 phage were precipitated with PEG and re suspended in SDS PAGE sample buffer (Laemmli, *Nature* 277, 680–685, 1970). Polypeptides from $1 \times 10^{12}$ pfu were fractionated on 12.5% polyacrylamide gel, then transferred electrophoretically to nitrocellulose paper (NCP)(Towbin, et al., *Proc. Natl Acad. Sci. USA* 76, 4350–4354, 1979). The NCP was incubated firstly in blocking buffer (4% bovine serum albumin [BSA] in phosphate buffered saline [PBS], 0.02% $NaN_3$), then with goat anti-mouse kappa light chain alkaline phosphatase conjugate (Southern Biotech). After washing NCP in PBS 0.05% Tween-20 (PBS/T) labeled polypeptides were revealed using a chromogenic substrate as described (Harlow & Lane, *Antibodies: A laboratory manual.* Cold Spring Harbor Laboratory Press, New York, 1988).

EXAMPLE 2

Phage Propagation

Phage panning experiments. Unless stated otherwise phage were propagated in *Escherichia coli* (strain XL1-blue, Stratagene) in Superbroth ([3-N-morpholino] propane-sulfonic acid, 10 g l$^{-1}$, Bacto tryptone, 30 g l$^{-1}$, yeast extract, 20 g l$^{-1}$, pH 7.0) at 37° C. in for 16 h, and recovered from the spent media using PEG-8000 as described (Sam brook, et al., *Molecular Cloning: A laboratory manual*, 1989). Multiwell removable strips (Maxisorp, Nunc) were coated overnight at room temperature (RT) with 100 µl/well PCMO-BSA, PHS-BSA, or goat anti-mouse kappa light chain IgG (Southern Biotech), each diluted to 10 µg ml$^{-1}$ in 0.1 M carbonate buffer (pH 9.6). The coating solution was replaced with blocking buffer and after 2 h at RT 100 µl of phage diluted in 0.1% BSA in PBS were added to duplicate wells and incubated for 3 h at RT. Wells were washed ×5 (5 min per wash) with PBS/T plus 0.1% BSA, and bound phage were eluted into 100 µl/well 0.1 M glycine (pH 2.2) for 15 min and neutralized by adding an equal volume of 1 M Tris-HCl (pH 8.0). In experiments requiring multiple rounds of phage panning against antigen the neutralized eluate was added to freshly prepared bacteria in order to generate phage required for the next round of he panning. Phage titer was assessed using standard methodology as described (Sam brook, et al., *Molecular Cloning: A laboratory manual*, 1989).

Oligonucleotide hybridization and plaque immunostaining procedures. Replicas of phage plaques were made by applying dry nitrocellulose filters (0.45 µm, Schleicher & Schuell) to agar plates. After 1 min filters were removed, air dried, then baked in a vacuum oven at 80° C. for 1 h. Filters were incubated in pre-hybridization buffer (0.25% non fat milk powder in 6×SSC) at 68° C. for 1 h. Two 15 bp oligonucleotides GAAGTAACGGTTGAC (SEQ ID NO:10) and GAAGTACCAGTTGAC (SEQ ID NO:11), designed to hybridize in a specific fashion to the DB3 R100 and W100 variants respectively, were end-labeled with digoxigenin using the Genius 5 3' end labeling kit (Boehringer Mannheim) according to the manufacturers instructions. Labeled probes were added to the filters in pre hybridization buffer and incubated at 25° C. for 4 h. After washing with fresh pre hybridization buffer the filters were first incubated in blocking buffer, then transferred to PBS/T containing alkalinephosphatase conjugated anti-digoxigenin antibodies (Boehringer Mannheim). In plaque immunostaining experiments, nitrocellulose plaque replicas on nitrocellulose were made as above except the filters were left on the plates for 2 h at 37° C. before removing and blocking as above. Blocked filters were incubated with alkaline phosphatase conjugated anti-mouse or anti-human k light chain antibodies (Southern Biotech). All filters were washed and developed as described for western blotting except in hybridization experiments the development was carried out overnight at 4° C.

Electron Microscopy. Stable complexes of 5 nm gold particles with PHS-BSA or goat anti mouse kappa chain were prepared essentially as described (Horisberger & Rosset, *J. Histochem. Cytochem.* 25, 295–305, 1977; Slot, & Geuze, *Eur. J. Cell Biol.* 38, 87–93, 1985). To ensure the removal of any unbound protein the complexes were centrifuged through a 7% glycerol cushion as described (Slot, & Geuze, *Eur. J. Cell Biol.* 38, 87–93, 1985). The pelleted complexes were resuspended in PBS containing 0.1% BSA and 0.02% $NaN_3$ and stored at 4° C. Phage were prepared at 25° C. with IPTG or at 37° C. without IPTG diluted into PBS containing 1% BSA and $2 \times 10^9$ pfu were applied to Formvar coated nickel grids (200 mesh). Unbound phage were removed by washing with PBS and then 1% BSA in PBS was applied for 10 min. Protein-gold complexes were centrifuged briefly (700×g, 2 min.), and applied to the grids undiluted (ca. 20 µg protein ml$^{-1}$). After 30 min. the grids were washed with PBS, then stained with 1% uranyl acetate for visualization by electron microscopy. All incubations were done at RT in a humid atmosphere. Randomly selected areas on the grids were photographed in order to quantify the number of gold particles associated with the phage.

The JC-M13-88 display vector was constructed by modifying M13mp18. The b-galactosidase a-complementation peptide encoding region was replaced with the ompA leader, antibody $V_H$/k and the synthetic gpVIII cassette as shown in FIG. 1.

Western blots of poly ethylene glycol (PEG)-precipitated antibody phage polypeptides probed with anti-mouse k light chain reagent revealed a single immunoreactive protein which migrated at ~47 kilodaltons (kDa), which is similar to the predicted molecular weight of the DB3 R100 $V_H$/k-gpVIII polypeptide (44,656 Daltons) Polypeptides from M13mp18 control phage were not immunoreactive. This finding confirmed that the DB3 $V_H$/k-gpVIII moiety was successfully integrated into the phage particle (or at least coprecipitated with phage). Phage prepared at 25° C. with IPTG induction were used to determine the density of the antibody on the filament surface by electron microscopy. The number of progesterone-11α-ol-hemisuccinate-bovine serum albumin (PHS-BSA) labels per phage varied from one (~34% phage) to four (~1% phage) adopting a classical distribution pattern. About 50% of the phage did not display functional antibody. Whilst phage prepared at 37° C. without IPTG, were essentially devoid of fusion and the few phage that could be observed binding antigen or binding to goat anti-mouse kappa chain were monovalent (3b&c). Preparations of wild-type M13mp18 phage were not labeled by either the PHS-BSA or the BSA gold probes. The effect of growth temperature and fusion induction by IPTG on antibody phage yield and subsequent enrichment by binding to immobillized steroid was investigated. Lower growth temperature resulted in lower overall phage production. Cultures grown for 6 h at 37° C. or 16 h at 30° C. had similar titers of phage (~$10^{12}$ plaque forming units (pfu) $ml^{-1}$), while cultures grown for 16 h at 25° C. resulted in a further ten fold reduction in titer. The addition of 1 mM IPTG to bacterial cultures reduced the final phage titer after equivalent growth periods by 3 to 4 fold. In a panning experiment with equivalent pfu of phage prepared at 25° C. with IPTG and at 37° C. without IPTG, a 100 fold difference was noted in the phage eluted (Table I).

TABLE I

| Growth conditions for DB3 R100 phage | Pfu Eluted[X#] (×$10^4$) | % pfu eluted/ pfu applied | Recovery factor[@] |
|---|---|---|---|
| 37° C. + IPTG | 5.58 (+/−0.3) | 0.0279 | 5.5 |
| 37° C. | 1.02 (+/−0.04) | 0.0051 | 1.0 |
| 30° C. + IPTG | 19.44 (+/−0.8) | 0.0972 | 19.1 |
| 30° C. | 5.18 (+/−0.2) | 0.0259 | 5.1 |
| 25° C. + IPTG | 113.96 (+/−11.2) | 0.5698 | 111.7 |
| 25° C. | 39.22 (+/−2.84) | 0.1961 | 38.5 |
| M13mp18* | 0.1 (+/−0.04) | 0.0005 | 0.1 |

[X]DB3R100 or M13mp18 phage were propagated using different growth conditions and 2×$10^8$ plaque forming units were applied to ELISA plates coated with either PCMO-BSA or BSA alone. After a fixed time interval the plates were washed and bound phage were eluted with acid and the output titer was determined.
*M13mp18 were propagated at 37° C. without IPTG.
Figures represent the mean average of plaque forming units eluted from two separate experiments corrected for non-specific binding to BSA (2860+/−1690). Values for the experimental error are shown in ( ).
@The quantity of phage eluted is shown relative to the DB3 R100 phage produced at 37° C. without IPTG, here assigned a value of 1.

Phage prepared at the lower temperature with IPTG appeared to enrich more efficiently in the panning process. The amount of antibody incorporated into the phage was analyzed by western blotting, The addition of IPTG slightly increased the amount of fusion polypeptide. In phage propagated at 37° C. we observed a small amount of an immunoreactive species of approximately 20 kDa. This is likely due to $V_H$/k-gpVIII polypeptide proteolysis during phage storage in which the $V_H$/$V_L$ has been cleaved. In phage prepared at 30° C. and 25° C. this band was was not detected. Phage prepared at the lower temperature also appeared to have increased antibody fusion incorporation.

The recombinant wild type steroid binding antibody fragment derived from DB3 encodes a tryptophan at position 100 of the VH domain and is designated W100. The two phage is W100 and R100 differ in two nucleotides which change the codon at position 100 of the VH domain of the displayed DB3 from tgg to cgt (arginine) respectively. The affinities of the recombinant DB3 $V_H$/k W100 and R100 variants for progesterone and related steroids were determined previously (W100 to PHS-BSA, Ka~$10^9$ $M^{-1}$, and to progesterone-3-carboxymethyloxime (PCMO)-BSA Ka~$10^7$ $M^{-1}$; the R100 mutant to PHS-BSA, Ka~$10^9$ $M^{-1}$, and to PCMO-BSA Ka~$10^{11}$ $M^{-1}$). However, the authors were not able to distinguish either DB3 variant by binding to PHS-BSA by competition enzyme-linked immunoadsorbent assay (ELISA). A mixture of the W100 and the R100 $V_H$/k phage was diluted into a 50,000-fold excess of a control phage (BR4) displaying a human $V_H$/k, and repeatedly panned on either progesterone PCMO-BSA, PHS-BSA or an anti-mouse kappa light chain antibody. A mock panning of the phage mixture was carried out with plates coated with unmodified BSA. The recovery of phage displaying murine (DB3) or human (BR4) $V_H$/k polypeptides was monitored by immunostaining of plaque replica filter lifts on nitrocellulose filters (Table II).

TABLE II

| | Enrichment factor[#] after panning on antigen | | |
|---|---|---|---|
| Rounds of panning* | PHS-BSA | PCMO-BSA | Anti-mouse kappa Light chain IgG |
| 0 | 1 | 1 | 1 |
| 1 | 580 | 730 | 640 |
| 2 | 8.1 × $10^4$ | 1.8 × $10^5$ | 4.3 × $10^4$ |
| 3 | 5.8 × $10^5$ | 2.6 × $10^6$ | 5.9 × $10^5$ |

*An equal mixture of the murine DB3W100 and R100 phage was diluted into a 50,000 fold excess of the control phage BR4, which displays a human $V_H$/κ antibody. ~1×$10^{10}$ mixed phage were used in panning experiments.
This figure represents the increase in the ratio of DB3 phage over BR4 phage in the eluted phage relative to the initial phage mixture (DB3:BR4=1:50,000), here assigned a value of 1. Phage were propagated at 37° C. without IPTG.

The proportion of DB3 phage within the phage mixture was enhanced by over 700 fold following a single round of panning on steroid coated plates. Further rounds of panning increased this proportion although the first round produced the most dramatic increase. This may be due to the saturation of available binding sites during latter rounds of panning by DB3 phage. We utilized two independent panning ligands to differentiate between selection based on steroid binding (i.e. a functional combining site) and on anti-kappa light chain binding (i.e. epitope recognition). However, the similar enrichment rate of DB3 phage over the control phage by panning on PHS and PCMO was paralleled by panning against anti-mouse k light chain antibodies. This provides a correlate that the majority if not all of the $V_H$/k molecules on the phage which the kappa epitope also retain steroid binding.

The proportion of phage encoding the DB3 R100 or W100 variants was determined by oligonucleotide hybridization to replica plaque filter lifts (Table III).

TABLE III

| | % DB3 R100 variant in phage eluted after panning on antigen[#] | | |
|---|---|---|---|
| Rounds of panning* | PHS-BSA | PCMO-BSA | Anti-mouse kappa Light chain IgG |
| 0 | 50+ | 50 | 50 |
| 1 | nd | nd | nd |
| 2 | 99.65 | 96.95 | 82.1 |
| 3 | 100 | 98.75 | 79.15 |

*A mixture containing equal numbers of the murine DB3W100 and R100 phage was diluted into a 50,000 fold excess of the control phage BR4, which displays a human $V_H$/κ antibody. ~1×$10^{10}$ mixed phage were used in panning experiments.
nd—Not determined—After one round of panning the ratio of the murine DB3:human BR4 was too small to permit accurate analysis of this value.
+The initial phage mixture used in this experiment contained an equivalent number of R100 and W100DB3 phage.
Figures represent the percentage of the murine DB3 phage eluted with the R100 mutation. Phage were propagated at 37° C. without IPTG.

In order to determine whether the enrichment was a function of steroid-ligand binding and/or a growth advantage of one DB3 variant over the other during propagation, a 1:1 mixture of the two phage in an excess of BR4 (human antibody phage) was panned against anti-mouse κ light chain antibodies. This enrichment being independent of steroid binding should permit other factors influencing phage display to be assessed. After two rounds of panning 82% of the DB3 phage were the R100 variant, this differential was maintained in subsequent round of panning. Although somewhat removed from the 50% figure expected, and probably due to a slight bias introduced in the early rounds of panning since the proportion difference did not increase in subsequent rounds. Whilst the proportion of R100 in the eluted phage was significantly greater following panning on both PHS and PCMO steroids and increased with each round of selection. Based upon our knowledge of the binding affinities of the DB3 $V_H$/κ variants for the different steroids, our observation that the R100 variant was preferentially enriched over W100 by panning on PCMO-BSA was not unexpected. However, a similar enrichment after panning on PHS-BSA implies that the DB3 R100 appears to have a slightly higher affinity for this ligand than the DB3 W100. The "mock" panning on BSA did not enrich for DB3 antibody phage over the control phage BR4, confirming that any potential growth advantage over the BR4 phage by either of the DB3 phage variants was not significant. Also, and despite exhaustive analysis of the recombinant phage by immunostaining of plaque replicas filter lifts made throughout the panning experiments, we did not observe loss of the $V_H$/κ gene. This finding suggests that single chain antibody likely inserts in JC-M13-88 appear to be stable.

What is claimed is:

1. A modified filamentous phage expression vector comprising a gene encoding a wild type major coat protein of the phage; a leaky, inducible promoter; a gene encoding a synthetic major coat protein of the phage; and a directional cloning site for receiving an insert that comprises a ribosome binding site encoding region, a leader sequence that directs polypeptide expression to a bacterial periplasmic membrane and a polypeptide encoding region, wherein the directional cloning site is situated between the promoter and the gene encoding the synthetic major coat protein of the phage wherein the vector is designated JC-M13-88.

2. A modified filamentous phage expression vector comprising a gene encoding a wild type major coat protein of the phage; a leaky, inducible promoter; a gene encoding a synthetic major coat protein of the phage; and a directional cloning site for receiving an insert that comprises a ribosome binding site encoding region, a leader sequence that directs polypeptide expression to a bacterial periplasmic membrane and a polypeptide encoding region, wherein the directional cloning site is situated between the promoter and the gene encoding the synthetic major coat protein of the phage wherein the vector has the sequence of SEQ ID NO:1.

* * * * *